(12) United States Patent
Crabb et al.

(10) Patent No.: US 7,845,814 B2
(45) Date of Patent: Dec. 7, 2010

(54) MARINE LED LIGHTING SYSTEM AND METHOD

(75) Inventors: Thomas M. Crabb, Middleton, WI (US); Robert C. Morrow, Madison, WI (US); Jeffrey C. Emmerich, Madison, WI (US); Marty Gustafson, Cross Plains, WI (US)

(73) Assignee: Orbital Technologies Corporation, Madison, WI (US)

( * ) Notice: Subject to any disclaimer, the term of this patent is extended or adjusted under 35 U.S.C. 154(b) by 150 days.

(21) Appl. No.: 12/258,897

(22) Filed: Oct. 27, 2008

(65) Prior Publication Data
US 2009/0140668 A1     Jun. 4, 2009

Related U.S. Application Data

(63) Continuation of application No. 11/689,698, filed on Mar. 22, 2007, now Pat. No. 7,473,008, which is a continuation of application No. 11/012,702, filed on Dec. 15, 2004, now Pat. No. 7,220,018.

(60) Provisional application No. 60/529,645, filed on Dec. 15, 2003.

(51) Int. Cl.
*F21V 33/00* (2006.01)
(52) U.S. Cl. .................. 362/101; 362/231; 362/267
(58) Field of Classification Search ............ 362/231, 362/101, 267
See application file for complete search history.

(56) References Cited

U.S. PATENT DOCUMENTS

| 3,066,645 A | 12/1962 | Mulder |
| 3,557,753 A | 1/1971 | Dantoni |
| 3,622,777 A | 11/1971 | Bovio |
| 3,805,740 A | 4/1974 | Hall |
| 3,913,526 A | 10/1975 | Hall |
| 4,059,072 A | 11/1977 | Vassallo et al. |

(Continued)

FOREIGN PATENT DOCUMENTS

CN     101187447     5/2008

(Continued)

OTHER PUBLICATIONS

Discussion Thread, "Anyone experimenting with LED lighting?"; http://fins.actwin.com/aquatic-plants/month.200108/msg00594.html, dated Aug. 24, 2001.

(Continued)

*Primary Examiner*—Ali Alavi
(74) *Attorney, Agent, or Firm*—Dorsey & Whitney LLP

(57) ABSTRACT

A method and apparatus of lighting a marine habitat for growth utilizing an LED light system. The light system includes an LED light source, a power supply for such light source and a controller for controlling the activation status and the intensity of the LED light source.

10 Claims, 4 Drawing Sheets

U.S. PATENT DOCUMENTS

| | | | |
|---|---|---|---|
| 4,084,905 | A | 4/1978 | Schreiber et al. |
| 4,268,894 | A | 5/1981 | Bartunek et al. |
| 4,697,374 | A | 10/1987 | Simms |
| 4,887,074 | A | 12/1989 | Simon et al. |
| 5,012,609 | A | 5/1991 | Ignatius et al. |
| 5,089,940 | A | 2/1992 | Lanzarone et al. |
| 5,165,778 | A | 11/1992 | Matthias et al. |
| 5,211,469 | A | 5/1993 | Matthias et al. |
| 5,278,432 | A | 1/1994 | Ignatius et al. |
| 5,345,305 | A | 9/1994 | Chen |
| 5,394,309 | A | 2/1995 | Brown |
| 5,614,378 | A | 3/1997 | Yang et al. |
| 5,660,461 | A | 8/1997 | Ignatius et al. |
| 5,799,124 | A | 8/1998 | Zorn et al. |
| 6,016,038 | A | 1/2000 | Mueller et al. |
| 6,065,849 | A | 5/2000 | Chen |
| 6,074,071 | A | 6/2000 | Baumberg et al. |
| 6,305,818 | B1 | 10/2001 | Lebens et al. |
| 6,340,868 | B1 * | 1/2002 | Lys et al. ............ 315/185 S |
| 6,474,838 | B2 | 11/2002 | Fang et al. |
| 6,523,976 | B1 * | 2/2003 | Turnbull et al. ......... 362/231 |
| 6,554,450 | B2 | 4/2003 | Fang et al. |
| 6,781,329 | B2 | 8/2004 | Mueller et al. |
| 6,921,023 | B1 | 7/2005 | Bright et al. |
| 6,921,182 | B2 | 7/2005 | Anderson, Jr. et al. |
| 7,220,018 | B2 | 5/2007 | Crabb et al. |
| 2002/0126504 | A1 | 9/2002 | Mansour |
| 2003/0137829 | A1 | 7/2003 | Ayers |
| 2005/0052883 | A1 | 3/2005 | Qi et al. |
| 2006/0035370 | A1 | 2/2006 | Lee et al. |
| 2007/0253196 | A1 | 11/2007 | Ormiston |
| 2007/0268693 | A1 | 11/2007 | Thomas et al. |

FOREIGN PATENT DOCUMENTS

| | | |
|---|---|---|
| DE | 42 18 880 | 7/1993 |
| DE | 4218880 | 7/1993 |
| DE | 200 20 352 | 2/2001 |
| DE | 20020352 | 2/2001 |
| DE | 202004008973 | 2/2005 |
| EP | 1 435 483 | 7/2004 |
| GB | 2239702 | 7/1991 |
| GB | 2416391 | 1/2006 |
| JP | 6319410 | 11/1994 |
| JP | 10162609 * | 6/1998 |
| JP | H8-333079 | 6/1998 |
| JP | 2003-61508 | 3/2003 |
| JP | 2003061508 | 3/2003 |
| JP | 2003-169566 | 6/2003 |
| JP | 2003169566 | 6/2003 |
| WO | WO 91/07641 | 5/1991 |
| WO | WO 91/18970 | 12/1991 |
| WO | WO 99/31560 | 6/1999 |
| WO | WO 00/50809 | 8/2000 |
| WO | WO 2004/109182 | 12/2004 |
| WO | WO 2005/059087 | 6/2005 |
| WO | WO 2005/065451 | 7/2005 |

OTHER PUBLICATIONS

Commercially available product known by the trade name: "Odyssea Second Generation Blue Moon LED Aquarium Light", producted by opposing attorney in a litigation case on Aug. 8, 2008.

Expert Report of Dana Riddle, filed in U.S. Dist. Ct. for the W. Dist. of Wisconsin on Nov. 3, 2008, case No. 08-C-220-C (appended therewith Exhibits A-B).

Expert Report of Dr. Sanjay Joshi, filed in U.S. Dist. Ct. for the W. Dist. of Wisconsin on Nov. 3, 2008, case No. 08-C-220-C (appended therewith Exhibits A-Q).

Expert Report of Tullio Dell Aquila, filed in U.S. Dist. Ct. for the W. Dist. of Wisconsin on Nov. 3, 2008, case No. 08-C-220-C (appended therewith Exhibits A-F).

Janssen, Marcel "Photosynthetic efficiency of *Dunaliella tertiolecta* under short light/dark cycles" *Enzyme and Microbial Technology* 29(2001) 298-305.

Kuykendall, Kevin. "MACNA Mania" (online) Reefkeeping Retrieved Feb. 1, 2010 from: http://reefkeeping.com/issues/2002-10/kk/feature/index.php 12 pages.

Zomick, Peter. "Tank of the Month, Jul. 2004." (online) Retrieve Feb. 1, 2010 from: http://reefkeeping.com/issues/2004-07/totm/index.php.

Advanced Aquarist's Online Magazine. "Featured Aquarium of Richard Ross." (online) Retrieved on Feb. 1, 2010 from http://www.advancedaquarist.com/issues/july2004/aquarium.htm.

Advanced Aquarist's Online Magazine. "Featured Aquarium of Ignasi Torralba." (online) Retrieved on Feb. 1, 2010 http://www.advanced aquarist.com/issues/nov2004/aquarium.htm.

Miracle Beam Tri-Lite Aquariam Lighting System, http://www.miraclebeam.com/trilite.asp, Oct. 1, 2003.

Miracle Beam Hi-Lite Aquarium Lighting System, http://www.miraclebeam.com/hilite.asp, Oct. 1, 2003.

Pacific Coast Marine Products Reef Lamp Plus Product, http://hoppingfish.com/products/reeflamp_plus.html, Oct. 1, 2003.

CustomSeaLife, Inc. PowerCompact/Moon-Light Aquarium Lighting System, http://cgi.ebay.com/ws/eBayISAPI.dII?ViewItem&item=2350202409&category=46314, Oct. 1, 2003.

Chuck Gadd, "*A Night-light for my Aquarium*" http://www.csd.net/~cgadd/aqua/art_nightlight.htm, Aug. 22, 2008.

Dana Riddle, "Effects of Narrow Bandwidth Light Sources on Coral Host and Zooxanthellae Pigments", http://advancedaquarist.com/issues/nov2003/feature.htm and "Joshi Image" means backroom jpg file, Mar. 16, 2002, http:/www.personal.psu.edu./faculty/s/b/sbj4/aquarium/new-pictures.

"Spectral Analysis of Recent Metal Halide Lamps: Shedding Some Light on New Reef Tank Illumination", Marine Fish USA & Reef, vol. 4, 2002, pp. 56-64.

http://www.apogee-inst.com/quantummeter_techinfo.htm, Jun. 1, 2008, 1 pg.

http://www.apogee-inst.com/bqm_spec.htm, Jun. 1, 2008, 1 pg.

* cited by examiner

Lightcode Basic Structure

Interface and Driver
Electronics Block Diagram

Quadrant System Components and Interconnects

Light Engine Base Assembly Details

MARINE LED LIGHTING SYSTEM AND METHOD

CROSS REFERENCE TO RELATED APPLICATION(S)

This application is a continuation of U.S. patent application Ser. No. 11/689,698, filed on Mar. 22, 2007, entitled "Marine LED Lighting System and Method" which is a Continuation of U.S. patent application Ser. No. 11/012,702, filed Dec. 15, 2004, now issued as U.S. Pat. No. 7,220,018, issued May 22, 2007 which claims benefit of U.S. Provisional Application No. 60/529,645, entitled "Aquarium Lighting System for Marine Growth," filed on Dec. 15, 2003, the subject matter of which are hereby incorporated therein by reference in their entirety.

BACKGROUND OF THE INVENTION

1. Field of the Invention

The present invention relates generally to a lighting system and method for marine growth and more specifically to a light-emitting diode-based (LED) lighting system that delivers programmable spatially and spectrally controlled light with the ability to provide optimal spectral output for sustenance and growth of marine life.

2. Description of the Prior Art

There are many lighting systems currently available that either promote growth for land-based plants or are used for decoration or illumination of marine life. However, none of the prior art describes a system for promotion of marine life using light-emitting diode based lighting.

Plant growth lighting systems and apparatus are common in many fields that include crop production, germination, tissue culture growth, horticulture, landscape architecture, and specialty growth systems. Although these systems provide for support of plant growth and development in terrestrial applications, none is suitable as a growth system for plants in aquatic settings. For productive growth, marine plants and animal life such as coral and algae require (at least in a limited manner) light of a specific intensity and within a specific range of wavelengths. Light quality and quantity are degraded as you go deeper in water which can preclude healthy sustenance at depths below a few feet without powerful lighting systems.

Marine growth apparatus are available for cultivating or permitting the growth of marine life. These systems typically consist of structures that provide a surface that permits the growth of coral, algae and other marine life, or provide a portable or permanent habitat for marine life to grow within. These include systems that are used for artificial coral reef development, coral reef regeneration, harvesting of marine life for food, and marine aquaculture for jewelry and ornamental aquariums. These inventions are typically passive apparatus that rely on natural solar light for illumination and do not use spatially or spectrally controllable artificial lighting to promote or accelerate growth.

Finally, aquarium lighting systems are also common and include light sources using fluorescent, incandescent, metal halide or light emitting diodes. These systems can be classified into two types. In type one, the primary purpose is to provide illumination to an underwater space. They contain a housing, light source within said housing, and means of power supply or connection to power supply. The light is not spatially controllable, but instead attempts to provide a consistent intensity above an area of the marine habitat. These systems use fluorescent, incandescent or metal halide light sources, which provide low intensity light with high radiant heat output and no user-defined spectral control. Maintenance is required on these systems (through light source bulb replacement) to maintain light intensity over time.

In type two, the primary purpose of the lighting system is to provide decorative lighting, including artificial moon light or colored lighting, to the marine landscape. These systems are not intended to provide sufficient quantity of light and are only supplemental to other light that supports healthy sustenance and growth. They contain a housing, a colored light source usually consisting of light-emitting diodes, lasers, color wheels or filters combined with a light source, or ultraviolet illumination, and a power supply or connection to power supply. They may or may not be portable or submersible systems that direct light at specific marine features.

Neither of these two types of marine lighting systems and apparatus is designed with an LED source offering spatial control of spectral output which can allow a user-defined or preprogrammed appropriate spectrum for growth of specific marine plant and animal life. Though the above are satisfactory for their designed applications, there is a continuing need for a marine lighting system that can be used to promote marine plant and animal life while offering the user spatial and spectral control.

DESCRIPTION OF THE INVENTION

The present invention provides a lighting system for marine growth and more specifically to a light-emitting diode-based (LED) lighting system that delivers spatially and spectrally controlled light with optional optimal spectral output for growth of marine life. Such systems are particularly applicable to photobioreactors, fish hatcheries and aquariums, among others. Improved growth is achieved due to user programmable spectral and spatial control of light to allow for organism-specific lighting conditions with optional portability and submergibility for even greater light intensity delivery.

LED lighting technology is able to deliver-high intensity light into a marine environment in a new way when compared to traditional systems. The use of LEDs enables the system to independently control the intensity of each spectral component as a function of time. This allows a user to provide the optimal wavelengths between 380 nm to 690 nm used by specific marine plant and animal life to support photosynthesis and/or optimum biological development. It provides a single controllable system which can also be used to simulate natural lighting conditions including sunrise, daylight, sunset and moonlight to provide a natural growth cycle, or to alter the lighting schedule to enhance growth during a particular phase of species development. Specific wavelengths can also be programmed to enhance the fluorescence and colors of certain species of fish and coral.

This system's LED lighting is provided with much greater intensity and lower radiant heat that traditional fluorescent-based lighting systems, changing the formerly high cooling requirements of a complete marine habitat. Another feature of this lighting technology, which is important for promoting and sustaining marine life, is that it does not experience degradation of wavelength with age as does fluorescent lighting. Fluorescent's loss of light intensity over time reduces the growth rate of certain species of marine life by minimizing the photosynthetic energy provided. These variations can also lead to the appearance of certain types of organisms such as cyanobacteria in marine habitats that occur as different light wavelengths are emitted from degraded fluorescent tubes.

In addition, LEDs are much more efficient than incandescent lamps and equal to or slightly more efficient that most fluorescent lamps. Safety of the system will also be improved due to low operating voltages and less heat dissipation. The lack of glass bulbs in the system when compared to all other light sources also improves safety by eliminating the explosive failure mode of previous systems.

Specific to the design of this system, the LED light engine can be housed in a waterproof system that, unlike traditional systems, can be submersed into the marine environment. The ability to secure high intensity lighting at any point within the environment enables light to be directed at marine life features that reside at depths far from surface top-mounted lighting. Marine plants and animals require specific light intensity for optimal growth. By providing a means to deliver light of greater intensity, lower power-usage and lower thermal delivery deeper in a tank than comparable overhead lighting, better growth of plant and animal life can be achieved at depths previously unable to sustain some types of marine growth.

In general, the system of the present invention includes LED lighting, a controller, a power supply, a light housing, and a cooling system. Optional software can be included to provide users with complete programmable control of spectral, spatial, intensity or pattern of light output. The LED lighting consists of small light engines that are configured into a non-submersible top or side lighting system, or used independently to create a submersible planar, point, or line source of light. The LED light engine consists of a cluster of light-emitting diodes, including both chip, organic and discreet LEDs dependent on the preferred embodiment of the system. The control system can be configured with or without closed loop control, and is the mechanism that allows for user or manufacturer programming of lighting period and pattern, spectral content, or spatial content of the light delivered. The cooling system uses either natural convection with the air to dissipate heat in a top-mounted lighting system, or through water cooling via conduction, forced water cooling or an air-water loop to cool the submersible lighting configurations.

DESCRIPTION OF THE PREFERRED EMBODIMENT

All of the preferred embodiments of the invention include a light source, a light source housing a power supply, a controller, connection cables, mounting hardware and (when necessary) cooling system.

Figure 1:
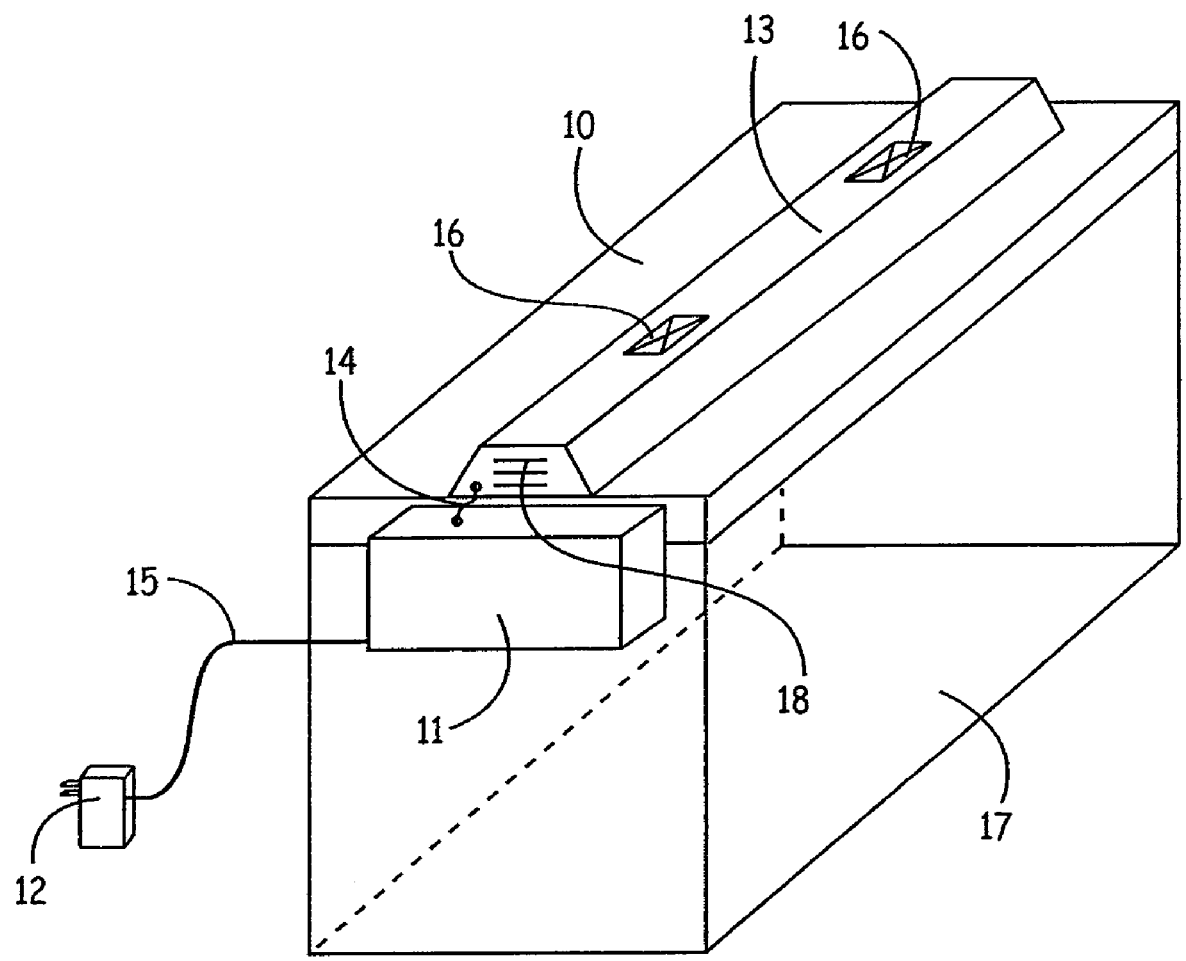
FIG. 1 is an isometric view of the marine lighting system in accordance with the present invention embodied in a top or side-mount configuration.

In the first embodiment, the lighting system is configured into a nonsubmersible light source as shown in FIG. 1. The use of LEDs for top-mounted lighting configurations produces a low profile size system when compared with current incandescent, fluorescent or metal halide-based lighting systems. In addition to its lower profile size, this configuration will operate with considerably less noise and radiant heat output than comparable fluorescent or metal halide systems.

In FIG. 1, the housing 10 is mounted to the top of a marine habitat and is connected to the controller 11 through a connection cable 14. The controller 11 can include an optional port for a user connection to a computer that will enable users, through software, to program spatial, spectral and intensity controls. The controller is then connected through a power cable 15 to either a low or high efficiency power supply 12 dependent on user options. Attached to the housing is a fan-based cooling system 13. The system 13 includes a fan housing with one or more fans 16 and a plurality of air inlet vents 18. During operation, the fans 16 draw ambient air through the vents 18 to cool the LED light sources within the housing 10. The housing 10 also includes mounting hardware for attachment of the housing 10 to the top or side of the marine habitat 17.

The controller 11, which will be described in greater detail below, can come preprogrammed into a spectral and spatial configuration to sustain and enhance marine plant and animal life, or the settings can be accessible by the user. The controller can be programmed into a closed loop system to react to local lighting, temperature, or other environmental factors. It can also provide one-way user-programmable control of the lighting period, the spectral content, the spatial control, or the intensity control.

Figure 2:
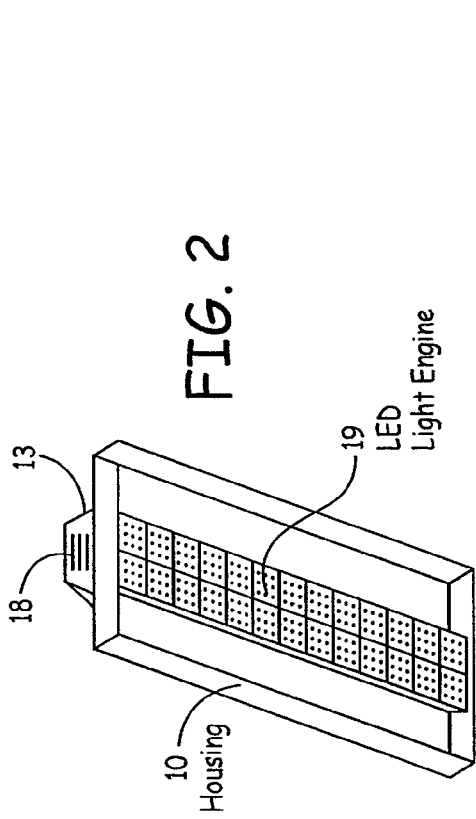
FIG. 2 is an isometric view of the light engine and configurable housing configuration of FIG. 1.

FIG. 2 shows a detail of the LED light engines 19 and housing 10. The light engines 19 are constructed on moveable components that allow a user to control their placement on the mounting bars of the light housing 10. A user can configure their overhead or side lighting to provide equal illumination and intensity across the entire top portion of the enclosure, or alternatively, to configure patterns or areas of greater light intensity.

Each of the light engines 19 is made up of a plurality or an array or cluster of individual LEDs. Each of the individual LEDs is capable of providing a predetermined variable intensity of light (depending on the applied power) at a predetermined wavelength when provided with a power source. In accordance with the present invention, the individual LEDs have intensity levels which, when combined in a light engine, provide a light engine 19 which is capable of producing light intensity of between 0 and about 1000 or more micromols per square meter per second, and more preferably between 0 and about 300 micromols per square meter per second. Each individual LED also preferably emits colors of light at a wavelength within the spectral range of 380 nm to 690 nm. In other words, each of the individual LEDs emits light of a wavelength in the red through the blue region of the spectrum. Although the preferred embodiment utilizes LEDs which emit light in the 380 nm to 690 nm region of the spectrum in the form of red, blue and/or green light emitting LEDs, LEDs emitting other colors could be utilized as well. The light engines, and in particular each of the individual LEDs, is driven by a power source which, in the preferred embodiment is 24 volts of direct current. The particular quantity of each type of LED in each light engine 19 depends on the marine life to be sustained. To sustain certain species of marine plant life, each engine might include at least about 50% red emitting LEDs and at least about 30% blue emitting LEDs.

Figure 3:
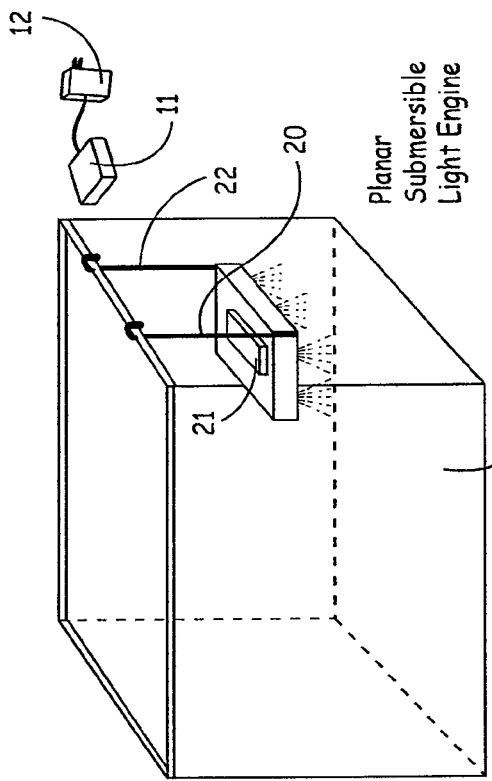
FIG. 3 is an isometric view of the marine lighting system embodied in a submersible planar light source configuration.

In the embodiment shown in FIG. 3, an LED light system comprised of one or more light engines has been mounted in a planar configuration, equivalent to those components used in the top and/or side mount configurations of FIGS. 1 and 2 to comprise a large overhead lighting system. In this case, a series of light engines is contained in a submersible, transparent watertight housing 20. The housing 20 is preferably combined with a heat circulation system 21. The system 21 includes water inlet and outlet ports to dissipate the heat from the LED via the surrounding water. Mounting hardware 22 is included to attach the housing 20 to the sides of the marine habitat 17. Attachment means may also be provided to attach to the housing 20 from the bottom of the habitat 17, or to suspend the housing 20 from the top of the habitat 17. This embodiment will allow for planar light distribution from any angle or depth into the marine environment. The intensity and spectral content of the light from the light engines can be controlled, via control of the individual LEDs within that light engine, to either specific requirements for a particular marine life or to simulate surface lighting at a lower depth.

Figure 4:
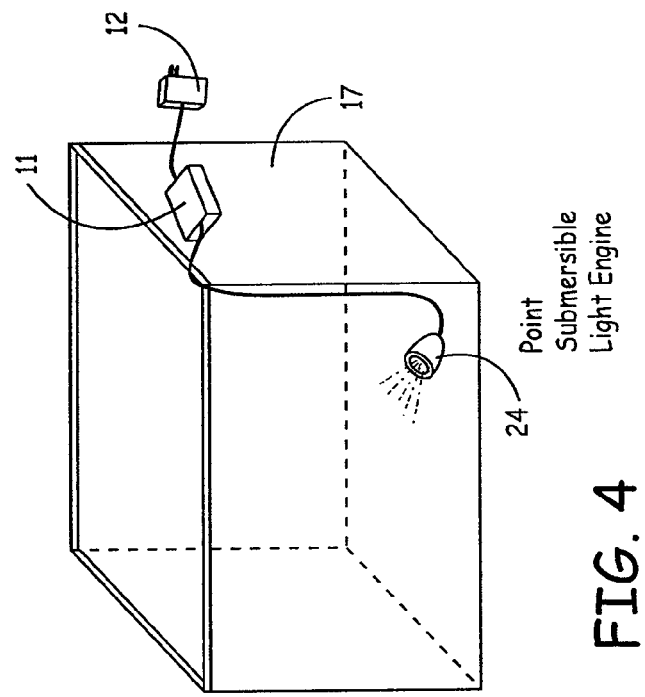
FIG. 4 is an isometric view of the marine lighting system embodied in a submersible point light source configuration.

In the embodiment shown in FIG. 4, an LED light cluster 24 has been mounted into a point configuration. It is contained in a submersible, transparent watertight housing. This light cluster 24 or light engine comprises a plurality or array of individual LEDs which are controlled or described. The housing may be combined with a heat circulation system to dissipate the heat from the light cluster 24 or engine out of the surrounding water. Mounting hardware is provided to attach the light to the sides of the habitat 17. Means may also be provided to attach the housing to the bottom or suspend it from the top of the habitat 17. This embodiment will allow for directed, controllable light to be isolated on a particular feature in the marine landscape that requires light of a specific intensity or wavelength to sustain or support its growth.

Figure 5:
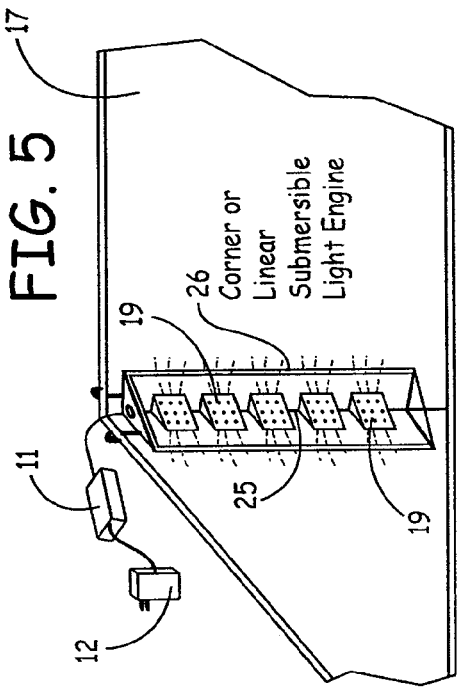
FIG. 5 is an isometric view of the marine lighting system embodied in a submersible linear or corner light source configuration.

In the embodiment shown in FIG. 5, a number of LED engines 19 have been mounted into a linear configuration on a mounting rail 25. The rail 25 is contained within a submersible, transparent watertight housing 26. The housing 26 is preferably combined with a heat circulation system to dissipate the heat from the LED out of the surrounding water. Mounting hardware is included and intended to provide attachment of the light along the sides of the marine habitat 17. This mounting system offers users the ability to light a section of the habitat along a depth or length and provide spatially or spectrally controlled lighting unobtrusively within the marine landscape.

The control for the light system of the present invention is designed to control the activation (on/off) status of each type of individual LEDs within each light engine and when activated (on), to control the intensity of each type of the individual LEDs within each light engine. Further, because each type of the individual LEDs emits its own particular wavelength of light, the spectral content or quality of each light engine is also controlled. In this way, both the intensity and the spectral content or quality of each light engine is controlled. More specifically, the control system is designed to provide independent control of the intensity of each spectral component as a function of time for selection of optimal wavelengths between about 380 nm to about 690 nm used by specific marine plant and animal life to support photosynthesis and optimal biological development.

The planar mounted design of FIGS. 1 and 2 is designed to provide a single controllable system to best simulate natural lighting conditions including such things as sunrise, daylight, sunset and moon light to provide a natural growth cycle for any marine life. Such a system may also be used to alter the lighting schedule to enhance growth during a particular phase of species development.

The submersible embodiments of FIGS. 3, 4 and 5 give the ability to provide high intensity lighting at any point within the habitat environment. This enables light to be directed at marine life that resides at depths far below the natural surface lighting or the top mounted lighting of FIG. 1. By providing submersible light sources such as shown in FIGS. 3, 4 and 5, better growth of plant and animal life can be achieved at depths previously unable to sustain some types of marine growth. With the submersible embodiments of FIGS. 3, 4 and 5, the lighting system can be integrated into a photobioreactor to create layers of light throughout a growing environment, effectively doubling or tripling the surface area for growth of organisms such as algae.

The basic system of construction is for a series of LED light engines to be spaced along each required one foot length. Preferably, each light engine contains a combination of individual LEDs, with each type of LED emitting its own particular wavelength, preferably between 380 nm and 690 nm. Each light engine preferably includes in excess of 100 total LEDs per square inch of light engine surface. The particular percentage of each type (i.e., wavelength type) of LEDs will depend on the specific marine life to be sustained and promoted. It is also contemplated that each light engine would also carry two photodiodes which may be used for closed loop light output control or as part of a plant growth detection/light engine engagement system.

Underwater lighting systems used for microalgae growth are also inherently subject to algae bloom or photosynthetic bacteria on the lighting surface. Therefore, a level of opaqueness may be experienced at different underwater light levels. This will dictate if the addition of a cleaning system is required by the user. If it is, the design can include the addition of low level ultra-violet LEDs to inhibit growth at the lighting surface without interfering with marine growth. Further, the housing used in the embodiments described above is produced with a non-leaching antibacterial plastic coating to inhibit growth at the lighting surface. As an alternative, the housing can be provided with a mechanical cleaning mechanism to periodically "wipe off" organisms from either an enclosed or non-enclosed lighting surface.

The control system preferably contains output controls and a main DC power supply to support a single light engine or a series of light engines. A microcontroller within the control assembly will read the control settings and the timer output and send appropriate signals to all light engines over the controller area network (CAN) bus.

On the outside of the control system, individual slider controls are provided to adjust the output irradiance of each spectral element independently. It will also include an illumination level control switch that will allow the user to manually select the number of light engines which are illuminated. A simple programmable digital timer may be provided to control day/night illumination cycles.

The power supply is a 1500 W, +24 Vdc power supply. The AC input for the power supply may be standard 120 Vac wall outlet power or 220 Vac at the users requirement. Twenty-four volt output power from the power supply will be routed to the power and signal distribution assembly. This assembly will provide the connection points to distribute power to each of the light engines as well as the required fusing. One low current fuse will be provided for each group of two light engines. In addition to power distribution the assembly will facilitate routing of the CAN bus signals to each of the light engines.

The interface electronics of the control system include control signals delivered over a two wire (CAN) bus from the main system controller to the light engine interface microcontroller. Command messages will control the number of light engines to be energized as well as the individual wavelength output intensities. Since each light engine can be individually controlled via control of its individual LEDs, the user is able to create lighting effects that mimic additional colors of light, including white, purple, etc. The driver electronics that control these individual selections consist of individual light engine selection switches and independent wavelength linear current drivers. Power to the driver electronics is provided by a two wire pair (+24 volt and ground) from the power and signal distribution assembly in the controller.

For those embodiments that have a fan/air cooled system, a small cooling fan will be mounted to the top of each light engine system. Air will be drawn from the bottom of each light engine system, through the internal cooling channel, over the driver electronics and exhausted through the top of the unit.

Figure 6:
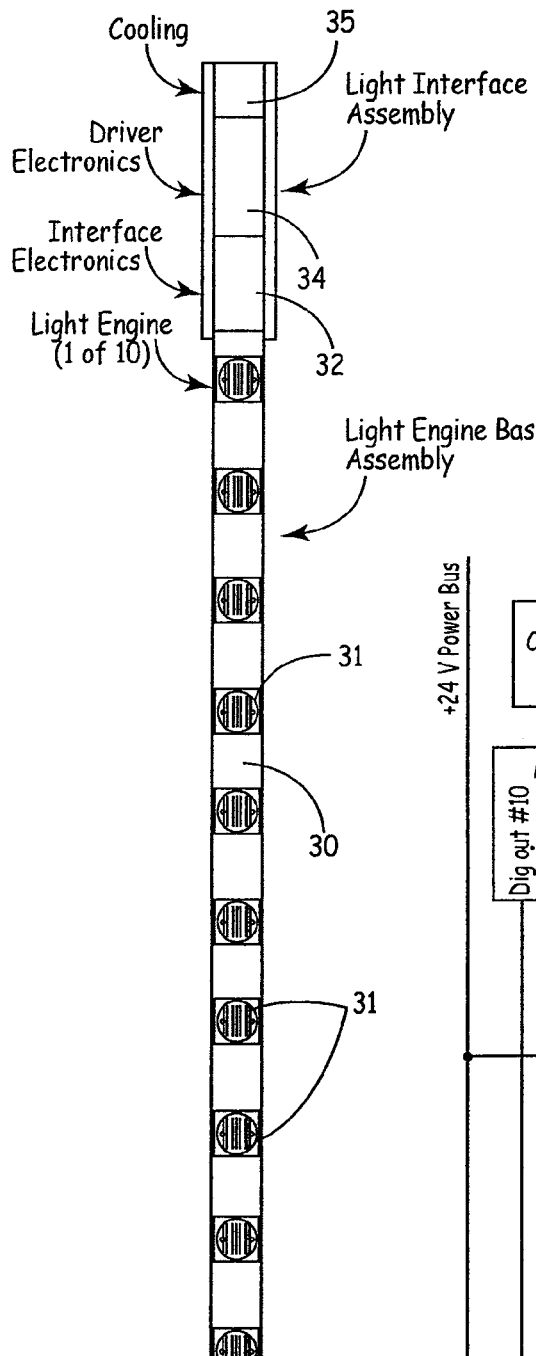
FIG. 6 is an elevational front view of a lighting system in accordance with the present invention with a plurality of vertically spaced light engines.

FIG. 6 shows the basic structure of a lighting system in accordance with the present invention with a series of vertically spaced light engines. Specifically, the structure of FIG. 6 includes a light engine base assembly 30 and a plurality of vertically spaced LED light engines 31. When used, the entire base 30 and the light engines 31 would be mounted within a housing having a substantially transparent surface. Because this is primarily an underwater or submersible structure, the housing would be watertight. The interface electronics 32, the driver electronics 34 and the cooling mechanism are provided at the top of the light engine base 30 as shown.

Figure 7:
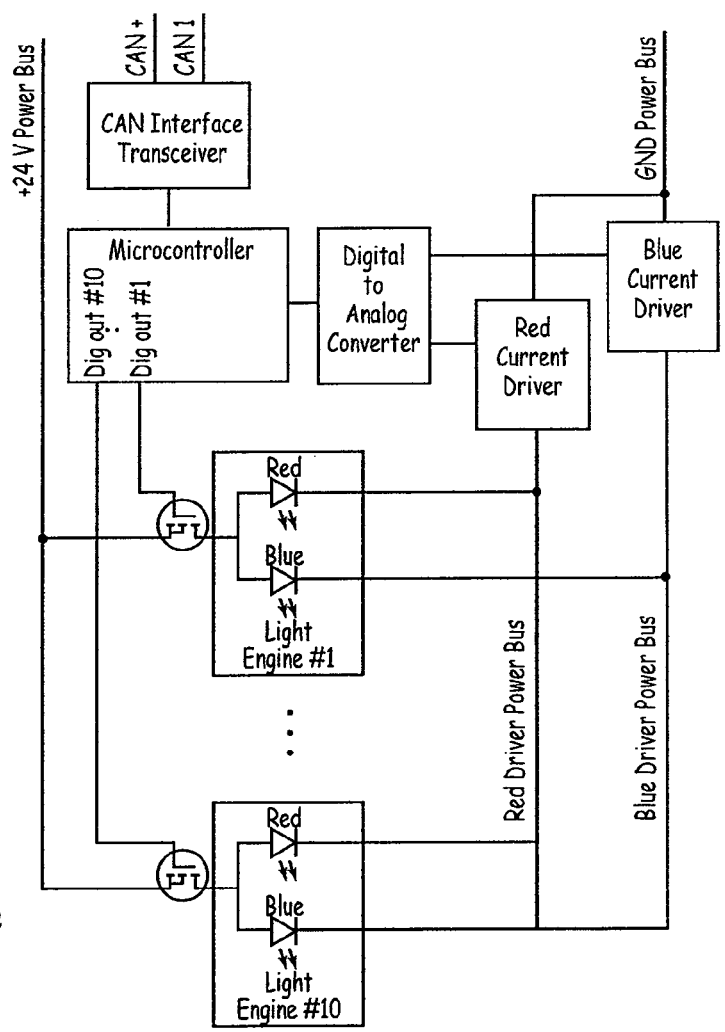
FIG. 7 is a block diagram for the controller interface and driver electronics.

FIG. 7 shows a block diagram for the control interface and driver electronics.

Figure 8:
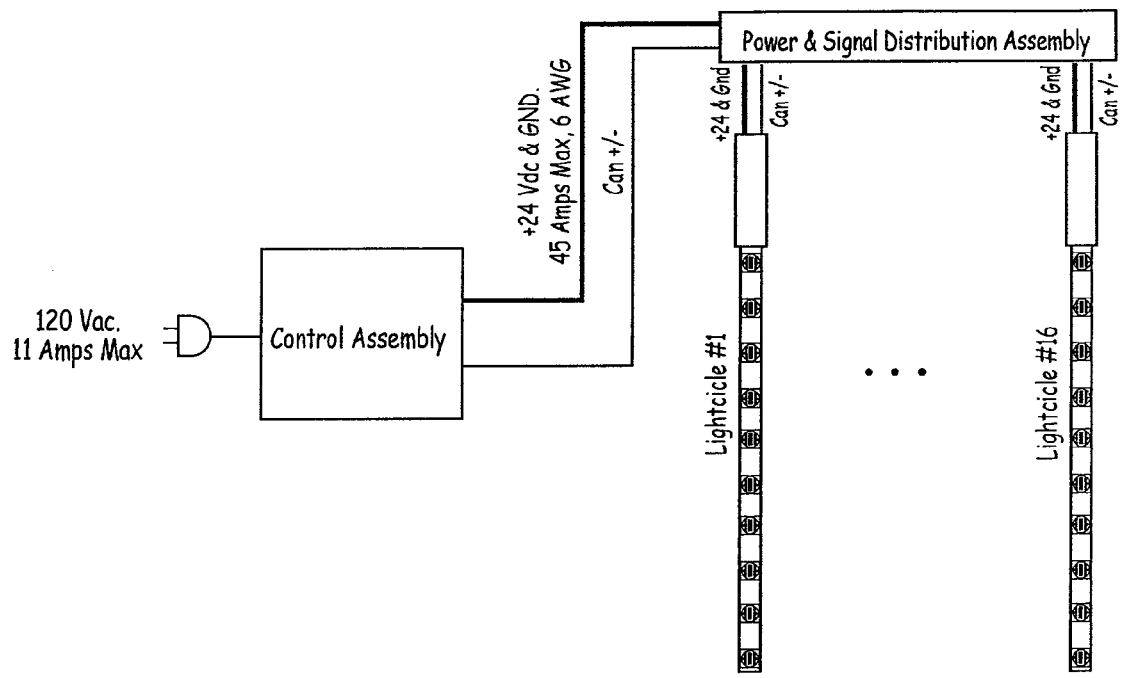
FIG. 8 is a view showing a lighting system in accordance with the present invention with a plurality of vertically oriented series of light engines.

FIG. 8 is a schematic diagram showing a control assembly and a powered signal distribution assembly for controlling a series of vertical LED light strips of the type shown in FIG. 6.

Figures 9, 10:
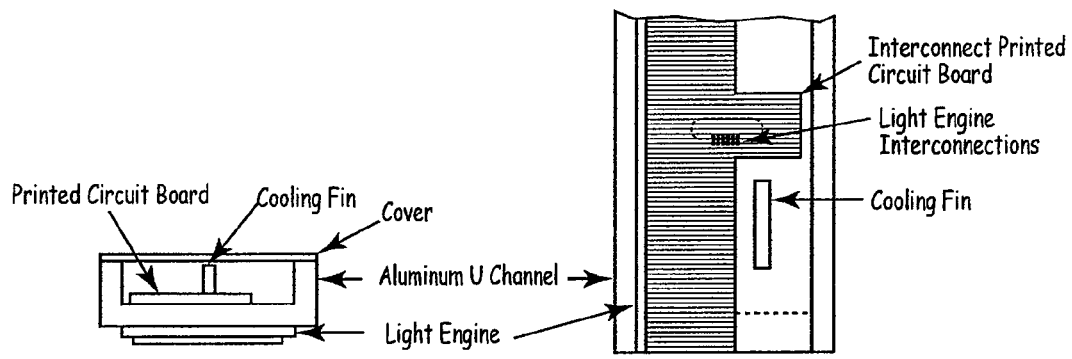
FIG. 9 is a top fragmentary view of a portion of a light engine base, with the cover removed.
FIG. 10 is an elevational end view of the light engine base shown in FIG. 9, with the cover in place.

FIG. 9 is a detailed view of a portion of the light engine base and connected light engine. Specifically, the base 30 is comprised of an aluminum U channel and includes a cooling fin, an interconnect for a printed circuit board and the interconnections with the light engine.

FIG. 10 is an end view of the light edge and base of FIG. 9 and shows similar elements.

Accordingly, the present invention is directed to an LED light system and method for controlling light to promote and/or sustain marine life (either plant or animal) in a marine habitat. The system includes one or more light engines mounted to a housing. If the system is designed to be submersible, the housing must be watertight. Each light engine is made up of a plurality or an array of individual LEDs (preferably at least 50 and more preferably at least 100). Each of these individual LEDs emits light at a particular wavelength, with all LEDs emitting a similar wavelength comprising a "type" of LED. In the preferred embodiment, these wavelengths are in the 380 nm to 690 nm range and comprise one of red, blue or green, although other colors could be used as well. Each type of LED within a light engine is capable of being activated (on) or deactivated (off) and, when activated, each type of LED is capable of having its intensity varied as a result of providing variable power.

Each light engine, and in particular each type of LED within a light engine, is operatively connected to a power source through a control system. The control system is designed to control each type of LED within a light engine, and thus control the light output of each light engine. Specifically, the control is designed to control the activation status (on/off) of each type of LED and, when activated, the intensity of each type of LED. In this way, the intensity and the spectral quality or content of each light engine can be controlled.

The method aspect of the present invention includes providing a housing with an LED light source mounted thereto. Such LED light source would preferably include one or more light engines made up of a plurality or array of individual LEDs as described above. The method would also include providing a power source and controlling the illumination of the light engines via controlling the activation status and the intensity of each type of LED therein.

The invention claimed is:

1. A combination marine habitat and lighting system, comprising:
   a marine habitat having an open top defined by a top edge; and
   a lighting system comprising:
      a housing connectable to the top edge being disposed submersible into the marine habitat; and
      an LED light source mounted to one side of the housing which is transparent watertight, the LED light source comprising at least one light engine having a plurality of individual LEDs.

2. The combination marine habitat and lighting system of claim 1, further comprising:
   a power supply sufficient to drive the LEDs; and
   a controller connected with the power supply for controlling activation status and intensity of one or more of the individual LEDs.

3. The combination marine habitat and lighting system of claim 1, wherein the housing is waterproof and the LED light source is mounted within the housing.

4. The combination marine habitat and lighting system of claim 1, wherein the LED light source, when activated, is sufficient to support marine growth.

5. The combination marine habitat and lighting system of claim 1, wherein the LED light source includes at least one of chip-based, organic or discreet LEDs.

6. The lighting system of claim 1, wherein the submersible housing is arranged in a planar configuration and is hung from the top edge of the open top of the marine habitat and disposed in parallel to the open top.

7. The lighting system of claim 1, wherein the submersible housing is arranged in a planar configuration and is hung from the top edge of the open top of the marine habitat and disposed vertically to the open top.

8. The lighting system of claim 1, wherein the submersible housing is arranged in a point configuration and disposed at bottom of the marine habitat.

9. The lighting system of claim 1, wherein the submersible housing is arranged in a planar configuration and suspended from the open top of the marine habitat.

10. The lighting system of claim 1, wherein the submersible housing is arranged in a point configuration and suspended from the open top of the marine habitat.

* * * * *